United States Patent
Harpaz

(10) Patent No.: US 9,833,414 B2
(45) Date of Patent: Dec. 5, 2017

(54) UNIFORMLY ABRASIVE CONFECTIONERY PRODUCT AND PROCESS THEREFOR

(75) Inventor: Shimon Harpaz, Netanya (IL)

(73) Assignee: Breezy Industries Ltd., Kiryat Arba (IL)

( * ) Notice: Subject to any disclaimer, the term of this patent is extended or adjusted under 35 U.S.C. 154(b) by 448 days.

(21) Appl. No.: 12/663,581

(22) PCT Filed: Jun. 10, 2008

(86) PCT No.: PCT/IL2008/000783
§ 371 (c)(1),
(2), (4) Date: Dec. 28, 2009

(87) PCT Pub. No.: WO2008/152626
PCT Pub. Date: Dec. 18, 2008

(65) Prior Publication Data
US 2010/0178352 A1    Jul. 15, 2010

(30) Foreign Application Priority Data

Jun. 10, 2007 (IL) .......................... 183818

(51) Int. Cl.
*A61K 9/50* (2006.01)
*A61K 8/11* (2006.01)
(Continued)

(52) U.S. Cl.
CPC .............. *A61K 9/5047* (2013.01); *A23G 3/50* (2013.01); *A23G 3/52* (2013.01); *A23G 3/54* (2013.01); *A23G 3/563* (2013.01); *A23L 33/10* (2016.08); *A23P 10/30* (2016.08); *A61K 8/11* (2013.01); *A61K 9/0056* (2013.01); *A61K 9/5078* (2013.01); *A61Q 11/00* (2013.01); *A61K 2800/28* (2013.01)

(58) Field of Classification Search
CPC .. A23G 3/50; A23G 3/54; A23G 3/563; A23L 33/10; A23P 10/30; A61K 2800/28; A61K 8/11; A61K 9/0056; A61K 9/5047; A61K 9/5078; A61Q 11/00
USPC .................................................. 424/490, 440
See application file for complete search history.

(56) References Cited

U.S. PATENT DOCUMENTS 3,687,691 A    8/1972  Adelstein
3,862,307 A    1/1975  Di Giulio
(Continued)

FOREIGN PATENT DOCUMENTS

EP    0060088        9/1982
EP    1762226   *   5/2007  ........... A61K 31/522
(Continued)

OTHER PUBLICATIONS

International Search Report and Written Opinion of PCT/IL2008/000783 dated Nov. 7, 2008 (11 pages).
(Continued)

*Primary Examiner* — Rachael E Bredefeld
(74) *Attorney, Agent, or Firm* — Rodney J. Fuller; Booth Udall Fuller, PLC

(57) ABSTRACT

The present invention relates to the field of confectionery products. More particularly, the invention relates to an abrasive confectionery product and a process for producing the same. The product comprises abrasive inclusions which are uniformly dispersed throughout a base material.

18 Claims, 5 Drawing Sheets

(51) Int. Cl.

| | | |
|---|---|---|
| *A61K 9/00* | (2006.01) | |
| *A23G 3/52* | (2006.01) | |
| *A23G 3/50* | (2006.01) | |
| *A23G 3/54* | (2006.01) | |
| *A23G 3/56* | (2006.01) | |
| *A23L 33/10* | (2016.01) | |
| *A23P 10/30* | (2016.01) | |
| *A61Q 11/00* | (2006.01) | |

(56) References Cited

U.S. PATENT DOCUMENTS

| | | | | |
|---|---|---|---|---|
| 4,384,004 | A | * | 5/1983 | Cea et al. ............... 426/3 |
| 4,513,012 | A | * | 4/1985 | Carroll et al. ............ 426/5 |
| 4,911,934 | A | * | 3/1990 | Yang et al. .............. 426/5 |
| 4,933,190 | A | | 6/1990 | Cherukuri |
| 5,226,197 | A | | 7/1993 | Nack |
| 5,266,335 | A | * | 11/1993 | Cherukuri et al. ........ 426/3 |
| 5,370,864 | A | | 12/1994 | Peterson |
| 5,525,352 | A | | 6/1996 | Kontos |
| 5,861,146 | A | * | 1/1999 | Peterson et al. .......... 424/65 |
| 5,993,805 | A | * | 11/1999 | Sutton et al. ............ 424/94.1 |
| 6,004,334 | A | | 12/1999 | Mythen |
| 6,083,489 | A | | 7/2000 | Fischer |
| 6,235,318 | B1 | * | 5/2001 | Lombardy et al. ........ 426/3 |
| 6,602,518 | B2 | | 8/2003 | Seielstad |
| 6,703,000 | B2 | | 3/2004 | Ning |
| 7,063,858 | B2 | | 6/2006 | Saniez |
| 7,067,150 | B2 | | 6/2006 | Farber |
| 2003/0124069 | A1 | | 7/2003 | Cornelius |
| 2003/0163149 | A1 | | 8/2003 | Heisinger |
| 2006/0024245 | A1 | | 2/2006 | Gebreselassie |
| 2006/0193909 | A1 | | 8/2006 | Stawski |
| 2006/0222683 | A1 | | 10/2006 | Mythen |
| 2006/0263413 | A1 | | 11/2006 | Boghani |
| 2006/0263414 | A1 | | 11/2006 | Pan |
| 2007/0042184 | A1 | * | 2/2007 | Coyne et al. ............ 428/402.2 |
| 2007/0054014 | A1 | | 3/2007 | Stawski |
| 2007/0134168 | A1 | | 6/2007 | Dodds |
| 2007/0166430 | A1 | | 7/2007 | Stawski |
| 2011/0232361 | A1 | | 9/2011 | Schlueter |

FOREIGN PATENT DOCUMENTS

| | | |
|---|---|---|
| GB | 2166651 | 5/1986 |
| WO | 98/37769 | 9/1998 |
| WO | 99/59427 | 11/1999 |
| WO | 01/80661 | 11/2001 |
| WO | 2005/030141 | 4/2005 |
| WO | 2005/058263 | 6/2005 |
| WO | 2005/102066 A1 | 11/2005 |
| WO | 2006/079343 | 8/2006 |

OTHER PUBLICATIONS

Seemann et al., (2001) Effectiveness of mechanical tongue cleaning on oral levels of volatile sulfur compounds. J Am Dent Assoc 132(9):1263-7; quiz 1318.

* cited by examiner

UNIFORMLY ABRASIVE CONFECTIONERY PRODUCT AND PROCESS THEREFOR

RELATED APPLICATIONS

This application is the U.S. national stage of PCT/IL2008/000783, filed Jun. 10, 2008, which claims priority to Israeli patent application no. 183818, filed Jun. 10, 2007, the contents of each of which are herein incorporated by reference for all purposes.

FIELD OF THE INVENTION

The present invention relates to the field of confectionery products. More particularly, the invention relates to a uniformly abrasive confectionery product and a process for producing the same.

BACKGROUND OF THE INVENTION

Confectionery products for addressing oral malodor are disclosed in the prior art. Some of these products provide abrasive surfaces which are intended for scraping the tongue to thereby dislodge microorganisms and their metabolites which contribute to malodor. Some confectionery products contain breath freshening substances and/or medicaments.

U.S. Pat. No. 6,004,334 discloses a tongue cleaning apparatus comprising a lozenge-shaped edible dissolvable candy having two sides of different compositions adhered by an edible adhesive. One side is a hard candy material having a pattern formed in it which is suitable for abrading the tongue, and the other side is a soft pliable candy material having a depression formed in its center to allow it to adhere by suction to the roof of the mouth.

U.S. Pat. No. 7,063,858 discloses a boiled sugar sweet with a rough texture, intended for the treatment of halitosis, comprising a crystalline ingredient, such as a powdered saccharide or an organic acid, wherein the crystalline ingredient exhibits a particle size of greater than 200 microns and a melting point of greater than 110° C.

U.S. Patent Application Publication No. 2003/0163149 discloses a breath freshener lollipop in which the edible applicator head has a textured surface and includes an antibacterial medicament for eliminating volatile sulfur compound precursors on the tongue. Medicaments disclosed are divalent elements, such as zinc or copper.

U.S. Patent Application Publication No. 2006/0222683 discloses a soft pliable dissolvable candy which provides tongue scraping action. According to the disclosure, a plurality of hard candy segments, preferably having raised ridges, are formed in one surface of the soft candy, and a plurality of depressions are formed in another side of the soft candy.

International Patent Application Publication No. WO 2005/102066 and U.S. Patent Application Publication No. 2006/0193909 disclose a pressed tablet having at least one abrasive surface suitable for cleaning the surface of the tongue. One disclosed product has different layers i.e. one surface being smooth and the other being abrasive, wherein the abrasive surface may be a formed uneven surface and/or may comprise abrasive particles embedded throughout a layer. Also disclosed is a pressed tablet without layers, formed of one composition and having abrasive inclusions wherein the latter comprise solid matrices, for example of carbohydrates or polyols, and may further include encapsulated or entrapped flavors and colors.

U.S. Patent Application Publication No. 2007/0054014 discloses a confectionery product for cleaning the surface of the tongue, the product comprising a first side and a second opposite side wherein the second side comprises an abrasive surface, and wherein the second side has a width and a length, the smallest of which is at least 1.6 times the product thickness. According to the disclosure, the product may be a deposited hard candy, but does not include a combination of soft and hard confectionery products. The disclosed abrasive surface may be provided by a formed uneven surface and/or may comprise abrasive particles incorporated into the composition, or located on the abrasive surface, or embedded in the abrasive surface. The disclosed inclusions are typically hard particles of at least 100 microns which are less soluble than the surrounding matrix, and may be made from solid matrices and extruded carbohydrates or polyols, and may further include encapsulated or entrapped flavors and colors.

The efficacy of such prior art products is limited by the period of time during which the hard regions or abrasions remain intact prior to being dissolved.

U.S. Patent Application Publication No. 2007/0134168 discloses a chewable oral composition for freshening the breath, such as a chewable candy, the composition comprising: (a) a water soluble bulk portion; (b) a gum base portion; and (c) a coating layer including fast release antimicrobial agent comprising a synergistic ratio of Magnolia Bark Extract and surface active agent. The disclosed antimicrobial agent may be encapsulated in a coated matrix or a biodegradable polymeric matrix.

U.S. Pat. No. 6,602,518 discloses a product including a medicament comprising: a consumable center, such as a hard center; and a compressible composition comprising an encapsulated medicament that is compressed around the consumable center.

U.S. Pat. No. 5,370,864 discloses a microcapsule suitable for reducing oral bacteria and providing breath protection comprising a shell material and a core composition comprising: (a) cetyl pyridium chloride; and (b) a sweetener component comprising: (1) acetosulfame; and (2) a second artificial sweetener selected from aspartyl peptide esters, sulfamide sweeteners, sulfimide sweeteners, dihydrochalcone sweeteners, ammoniated glycyrrhizins and mixtures thereof, wherein the ratio by weight of (1) to (2) is from about 1:15 to about 15:1.

U.S. Pat. No. 4,933,190 discloses a sweetener delivery system for incorporation into a chewing gum composition, the sweetener delivery system comprising a first coating formed from the combination of an emulsifier with low molecular weight polyvinyl acetate and a second outer coating prepared from a hydrophilic polymer.

Such prior art products may mask breath malodor but do not address removal of tongue coat substances which are the source of the malodor.

It would therefore be desirable to provide a long lasting abrasive confectionery product which further incorporates a medicinal health enhancing ingredient.

SUMMARY OF THE INVENTION

The present invention provides an abrasive confectionery product for addressing oral malodor. The product comprises abrasive inclusions or particles which are uniformly incorporated throughout the base material of the product and which provide a plurality of abrasive surfaces which are exposed as the base material dissolves during the course of consumption by the user. The confectionery product may further comprise a health enhancing agent, which when present, does not detract from the taste of the confectionery product. The invention further provides a process for producing an abrasive confectionery product that comprises a health enhancing agent.

In a first aspect, the present invention provides an abrasive confectionery product comprising a base confectionery material and a plurality of abrasive inclusions, wherein the abrasive inclusions are substantially uniformly dispersed throughout said base material.

As used herein, the term "substantially uniformly dispersed throughout said base material" and related grammatical constructions mean that the distribution of the abrasive inclusions within the base material is substantially even or similar in all regions therein, and that there is no particular region in the base material in which the concentration or proportion of the abrasive inclusions is substantially greater or lesser as compared to any other region therein.

There is no particular limitation on the shape of the abrasive inclusions, nor is there any requirement that they have a uniform shape or size. In particular embodiments, the abrasive inclusions have a shape selected from the group consisting of spherical and ellipsoid. When ellipsoid, the elongated axis of the abrasive inclusion may be referred to as the major axis. The diameter or major axis of the abrasive inclusion has a length ranging from 100 to 900 microns At this optimal size range, the abrasive inclusions are sufficiently large to apply a pressure onto the dorsum of the tongue, yet are sufficiently small to apply to the dorsum a localized pressure, rather than a wide-area pressure, which is suitable for effecting an abrading action.

Without wishing to be bound by any theory or mechanism of action, the abrading action resulting from a reciprocating movement in any desired direction of the abrasive inclusions onto a tongue surface, in particular the dorsal surface of the posterior region of the tongue, facilitates the loosening and removal of substances accumulated thereupon, including food debris, undesirable microorganisms and metabolic products thereof, thereby reducing sources of malodor within the oral cavity. The abrasive inclusions dissolve at a rate which is slower than that of the base material, thereby prolonging the length of time that the abrasive material is in the oral cavity.

In a particular embodiment, the abrasive inclusions are dissolvable in at least one of the oral cavity and the gastrointestinal tract. In one embodiment, the abrasive inclusions are dissolvable within the oral cavity. In one embodiment, the abrasive inclusions are dissolvable within the gastrointestinal tract.

In a currently preferred embodiment, the abrasive inclusions comprise microcapsules, wherein the microcapsules comprise a shell and a core. In one embodiment, the abrasive inclusions consist essentially of microcapsules, wherein the microcapsules comprise a shell and a core.

In a particular embodiment, the shell of the microcapsules is sufficiently hardened to provide an abrading action with respect to a tongue surface without causing damage or pain to the tongue surface.

In various embodiments, the shell of the microcapsule is dissolvable within the oral cavity or dissolvable within the gastrointestinal tract.

The microcapsule shell may be further coated with sugar or a substance flavored to have substantially the same taste as the base material.

In one embodiment, the confectionery product may further comprise a health enhancing agent. In a currently preferred embodiment, the health enhancing agent is contained in the core of the microcapsules. The health enhancing agent may be a pharmaceutical active agent or a natural product such as a herbal extract. In one embodiment, the health enhancing agent has activity in reducing, preventing or treating a disorder of the oral cavity. In one embodiment, the disorder of the oral cavity is selected from the group consisting of candidiasis, halitosis, herpes simplex, lichen planus, leukoplakia, stomatitis and xerostomia. In one embodiment, the stomatitis is aphthous stomatitis.

In one embodiment, the health enhancing agent is selected from the group consisting of an analgesic agent, an antibacterial agent, an antiseptic agent, a cholinergic agent, an antifungal agent, a steroid, a nutritional supplement, an ethereal oil, a vitamin, a plant product and combinations thereof.

In one embodiment, the shell of the microcapsules comprises a material selected from the group consisting of wax, shellac, starch, zein protein, ethyl cellulose, methylcellulose, hydroxypropyl methylcellulose, ethylacrylate, methacrylic acid copolymers and combinations thereof. In one embodiment, the shell comprises a combination of hydroxypropyl methylcellulose and ethyl cellulose.

According to one embodiment, the shell of the microcapsules is resistant to degradation upon exposure to high temperature, for example 70° C. to 130° C., and yet is capable of dissolving under conditions present in the oral cavity, for example at a temperature of 30° C. to 40° C. According to yet another embodiment, the shell of the microcapsule remains intact within the oral cavity and is capable of dissolving under conditions present in the gastrointestinal tract, for example in the stomach or small intestine.

In one embodiment, the shell is a thermal barrier for heat-sensitive materials contained in the core of the microcapsules. According to this embodiment, such heat-sensitive material(s) are protected against the deleterious effects of high temperatures used during the production of the confectionery product. This property of, the microcapsule shell enables incorporation into the confectionery product of health enhancing agents which are generally susceptible to degradation or inactivation upon exposure to heat, and which in the absence of the microcapsule shell would be rendered inactive if exposed to the temperatures used for producing the confectionery product. Further, the use of such heat-resistant microcapsules enables their incorporation into the base confectionery material in a substantially uniformly dispersed manner. That is, the microcapsules may be thoroughly mixed into and distributed throughout said base material while the base material is in a heated pliable state.

In one embodiment, the core of the microcapsules comprises an inert substrate. In one embodiment, the inert substrate comprises a material selected from the group consisting of lactose, sucrose, dextrose, maltodextrin, starch, microcrystalline cellulose, dicalcium phosphate, hydroxyapatite, tricalcium phosphate, talc, mannitol, xylitol, sorbitol, cyclodextrin and combinations thereof. In one embodiment, the core of the microcapsules consists essentially of an inert substrate.

The confectionery product may be selected from the group of a boiled sugar confectionery product, a non-caloric or reduced calorie confectionery product, and a toffee confectionery product.

The confectionery product may comprise a stick or handle embedded within the base material.

In one embodiment, the confectionery product consists essentially of the base confectionery material and the microcapsules, wherein a health enhancing agent is contained in the core of the microcapsules.

In one embodiment, the base confectionery material comprises at least one material selected from the group consisting of glucose, sucrose, sorbitol, xylitol, sucralose, isomalt, maltitol, polydextrose, a colorant, a flavorant, an acidulent and combinations thereof.

In another embodiment, the confectionery product further comprises at least one powder compartment wherein the at least one powder compartment comprises an effervescent agent. In one embodiment, the powder compartment is a powder center. In one embodiment, the effervescent agent is selected from the group consisting of sodium bicarbonate, potassium bicarbonate, sodium carbonate, potassium carbonate, calcium carbonate, ammonium carbonate and combinations thereof. In one embodiment, the effervescent agent is sodium bicarbonate.

In one embodiment, the confectionery product comprising at least one powder compartment further comprises at least one health enhancing agent. In one embodiment, the at least one health enhancing agent is contained in at least one of the core of the microcapsules and the powder compartment. In one embodiment, a powder center contains the at least one health enhancing agent. In one embodiment, different health enhancing agents are contained in the core of the microcapsules and in the powder compartment. In one embodiment, different health enhancing agents are contained in the core of the microcapsules and in the powder center In another aspect, the present invention provides a process for producing an abrasive confectionery product, wherein the abrasive confectionery product comprises a base confectionery material and a plurality of abrasive inclusions, the process comprising a step (a) dispersing the abrasive inclusions throughout said base material in a substantially uniform manner. In one embodiment, step (a) comprises thoroughly mixing together the abrasive inclusions and the base material, wherein said base material is in the form of a cooked mass, and wherein the mixing is carried out while the base material is maintained at a temperature in the range of 70° C. to 90° C., thereby providing a base material having the abrasive inclusions substantially uniformly dispersed therein.

In a currently preferred embodiment of the process disclosed herein, the abrasive inclusions comprise microcapsules, wherein the microcapsules comprise a shell and a core.

In one embodiment, the base confectionery material comprises at least one material selected from the group consisting of glucose, sucrose, sorbitol, xylitol, sucralose, isomalt, maltitol, polydextrose, a colorant, a flavorant, an acidulent and combinations thereof.

In one embodiment, the process further comprises a step (b) adding at least one material selected from the group consisting of a colorant, a flavorant, an acidulent and combinations thereof to the mix of the base material and abrasive inclusions.

In one embodiment, the process further comprises step (c) forming uniformly sized units from the base material having the abrasive inclusions substantially uniformly dispersed therein.

In one embodiment, the process further comprises step (d) inserting a powder formulation to at least one region of the base material having the abrasive inclusions substantially uniformly dispersed therein, wherein step (d) is carried out prior to step (c).

In one embodiment, the at least one region comprises the center region of the base material having the abrasive inclusions substantially uniformly dispersed therein. In one embodiment, the at least one region comprises random regions within the base material having the abrasive inclusions substantially uniformly dispersed therein.

In one embodiment, the powder formulation comprises an effervescent agent. In one embodiment, the effervescent agent is selected from the group consisting of sodium bicarbonate, potassium bicarbonate, sodium carbonate, potassium carbonate, calcium carbonate, ammonium carbonate and combinations thereof. In one embodiment, the effervescent agent is sodium bicarbonate.

In one embodiment of the process disclosed herein, the confectionery product comprises at least one health enhancing agent. In one embodiment, the microcapsules comprise an inert core. In one embodiment, the at least one health enhancing agent is contained in at least one of the core of the microcapsules and the powder formulation. In one embodiment, different health enhancing agents are contained in the core of the microcapsules and in the powder formulation.

DETAILED DESCRIPTION OF THE INVENTION

Definitions

Figure 1:
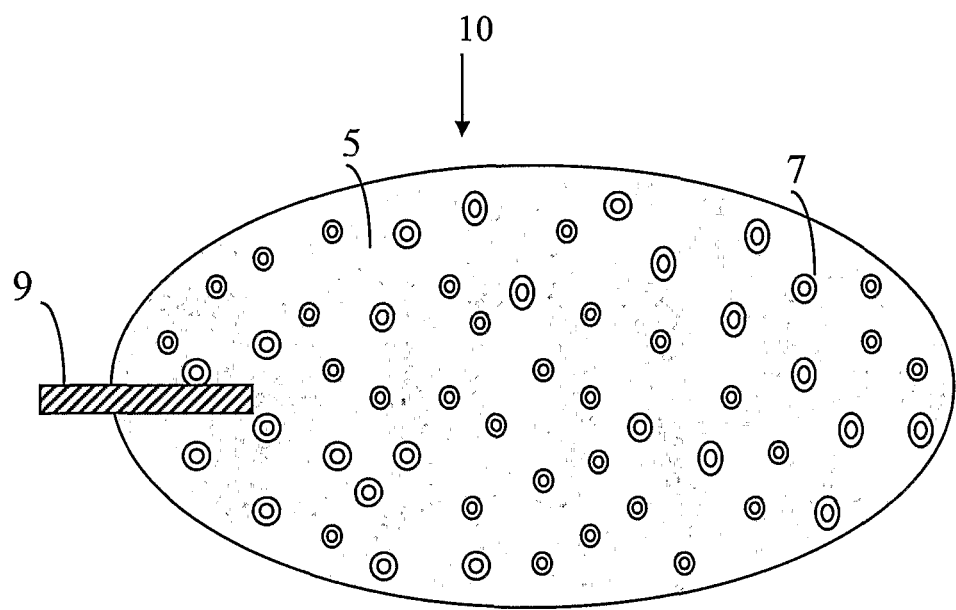
FIG. 1 is a cross sectional view of an abrasive confectionery product according to one embodiment of the invention.

As used herein, the term "substantially uniformly dispersed throughout said base material" and related grammatical constructions mean that the distribution of the abrasive inclusions within the base material is substantially even or similar in all regions therein, and that there is no particular region in the base material in which the concentration or proportion of the abrasive inclusions is substantially greater or lesser as compared to any other region therein.

As used herein, the term "abrasive" refers to the ability of the confectionery product of the invention to scrub and remove odor causing substances from surfaces within the oral cavity, including the tongue, in particular the dorsal surface, cheeks and palate, as the product is manipulated throughout the oral cavity by the user.

As used herein, the term "abrasive inclusions" refers to hard particles uniformly distributed within the base material of the confectionery product which are exposed to surfaces of the oral cavity as the base material dissolves. The abrasive inclusions are effective for scrubbing the tongue, in particular the dorsal surface, and other parts of the oral cavity so as to remove odor causing substances deposited thereupon.

As used herein, the term "uniformly abrasive confectionery product" refers to a confectionery product in which abrasive inclusions are substantially uniformly dispersed throughout a base material. The term however, does not require that the abrasive inclusions be of uniform size or shape.

As used herein, the term "microcapsules" refers to pellets or granules having a solid or liquid core enclosed in a coating. The coating may also be referred to as the shell. As is known in the art, various types of microcapsule structures can be obtained depending on the manufacturing process, e.g. mononuclear spherical, multinuclear spherical, multinuclear irregular, encapsulated mononuclear capsules, dual-walled microcapsules, ellipsoid, etc, all of which are encompassed by the present invention. The microcapsules of the present invention have a size between about 1 and about 2000 microns, for example between about 100 and about 900 microns, or between about 70 and 500 microns, or between about 50 and 400 microns.

The term "microencapsulation" as used herein refers to enclosure or encasement of substances in an outer coating or shell. Microencapsulation is a means of applying coatings to small particles of solids or droplets of liquids and dispersions. The materials micro encapsulated and surrounded by the shell may be termed the core. Typical equipment used to form microcapsules includes a conventional pan, a modified perforated pan and a Wurster coater.

The terms "base confectionery material" and "base material" are used herein interchangeably to refer to the candy material which forms the bulk of the confectionery product disclosed herein and is the medium in which the abrasive inclusions are substantially uniformly dispersed. The base material may comprise sucrose and glucose, as in standard confectionery products known in the art, or may comprise "sugar-free" or "reduced-calorie" substitutes known in the art, such as sorbitol, xylitol and the like.

As used herein, the term "dissolvable" and related grammatical forms mean that a substance, such as the shell of the microcapsules disclosed herein characteristically changes from a solid state to a liquid or semi-liquid state upon exposure to particular conditions, either in the presence or absence of a liquid. For example, a microcapsule shell may be dissolvable at a certain temperature range and/or pH range.

As used herein, the term "powder compartment" means a section or region of the confectionery product that is formed from a powder. A powder contains finely divided particles, having a size in the range of less than about 500 microns, for example about 100 to about 200 microns.

As used herein, the term "effervescent agent" refers to a substance that releases a gas upon contact with aqueous liquid.

As used herein, the singular forms "a", "an" and "the" include plural forms unless the context clearly dictates otherwise. Thus, for example, reference to a "health enhancing agent" includes combinations of health enhancing agents, and so on.

According to the invention, the abrasive inclusions which are uniformly dispersed throughout the base material of the confectionery product may be made from a number of different materials, including crystalline sugars or polyols; solid matrices (such as from fluid bed coating or spray drying) of carbohydrates, polyols or combinations; or extruded carbohydrates, polyols, or combinations; granular food acids; granular inorganic edible salts, such as calcium phosphate salts and other calcium salts including calcium lactate, calcium carbonate and calcium gluconate, silica, silicate salts and bicarbonates; and combinations thereof.

There is no particular limitation on the shape of the abrasive inclusions. In particular embodiments, the abrasive inclusions have a shape selected from the group consisting of spherical and ellipsoid. Ellipsoid shapes have at least one axis elongated as compared to the other two axes, and include for example oblate (disc-like) and prolate (cigar-like) spheroids. When ellipsoid, the elongated axis of the abrasive inclusion may be referred to as the major axis. The diameter or major axis of the abrasive inclusion has a length ranging from 100 to 900 microns or between about 70 and 500 microns, or between about 50 and 400 microns. It is to be expressly understood that the abrasive inclusions may be uniform in size and/or shape but there is not particular requirement that they be uniform in size and/or shape.

FIG. 1 illustrates a cross sectional view of an abrasive confectionery product according to one embodiment of the invention, which is designated as numeral 10. As shown, confectionery product 10 comprises base confectionery material 5; a plurality of abrasive inclusions, corresponding to microcapsules 7 which are substantially uniformly dispersed throughout base material 5; and optionally, stick 9 embedded within base material 5 when confectionery product 10 is a lollipop. According to this embodiment, microcapsules 7 comprise a core and a shell, wherein a health enhancing agent is contained within the core. Since they are substantially uniformly dispersed throughout base material 5, microcapsules 7 within confectionery product 10 are exposed to the oral cavity as abrasive inclusions as base material 5 is incrementally dissolved. Confectionery product 10 may assume any suitable shape, size, and weight. An exemplary weight of confectionery product 10 ranges from 9-15 g.

The diameter or major axis of microcapsules 7, whether having a spherical or ellipsoidal configuration, or any other desired configuration, has a length ranging between about 100 and 900 microns, or between about 70 and 500 microns, or between about 50 and 400 microns. At this optimal size range, microcapsules 7 are sufficiently large to apply a pressure onto the dorsum of the tongue, yet are sufficiently small to apply to the dorsum a localized pressure, rather than a wide-area pressure, which is suitable for effecting an abrading action. The abrading action resulting from a reciprocating movement in any desired direction of the microcapsules onto the dorsum facilitates the loosening of substances which may be the source of oral malodor, including food debris, microorganisms, and metabolic products thereof. These substances are then removed from the oral cavity as they are swallowed by the user in the course of mastication and saliva production as the confectionery product is consumed.

Microorganisms associated with oral malodor include anaerobic bacteria, which subsist under a protective layer of mucous, food particles and proteins, such as in the fissures and mucous layer on the dorsal surface of the tongue, and create waste products known as volatile sulphur compounds (VLC). VLC are believed to be a contributing cause of halitosis. In addition, yeast and fungi e.g. Candida albicans, which can cause disorders of the oral cavity such as candidiasis are associated with oral malodor.

The use of a stick 9 allows confectionery product 10 to be selectively positioned on the pharyngeal part of the tongue, which faces the oropharynx, in order to effect an abrading action thereon, without inducing the gag reflex normally caused by contact with the pharynx.

In addition to being able to alleviate halitosis by means of a mechanical abrading action, confectionery product 10 is also advantageously able to improve oral hygiene. The microcapsules 7 exposed to the oral cavity may dissolve, thereby releasing a health enhancing agent which is conducive to oral hygiene. Those microcapsules 7 that have been separated from base material 5 and have not dissolved will be swallowed, and will release the health enhancing agent upon dissolving in the gastrointestinal tract.

When the confectionery product is a boiled sugar confectionery product, microcapsules 7 occupy a volume in the range of about 20% or less, or about 10% or less, or about 5% or less that of confectionery product 10, excluding stick 9, when a stick is in use. In one exemplary embodiment, base material 5 comprises the following ingredients, at the indicated concentrations with respect to the confectionery product 10: sugar (i.e. sucrose) 50-60%; glucose 40-50%; moisture 0.1-1%; citric acid 0.1-1%; odorants and flavorants 0.5-1%; and colorants 0.2-0.8%.

Confectionery product 10 may also be a reduced-calorie or non-caloric confectionery product which comprises a sugar substitute well known to those skilled in the art as a sweetener. Examples of sugar substitutes include for example, sorbitol, xylitol, sucralose, isomalt, maltitol and polydextrose. The confectionery product may alternatively be a toffee confectionery product.

Figure 2:
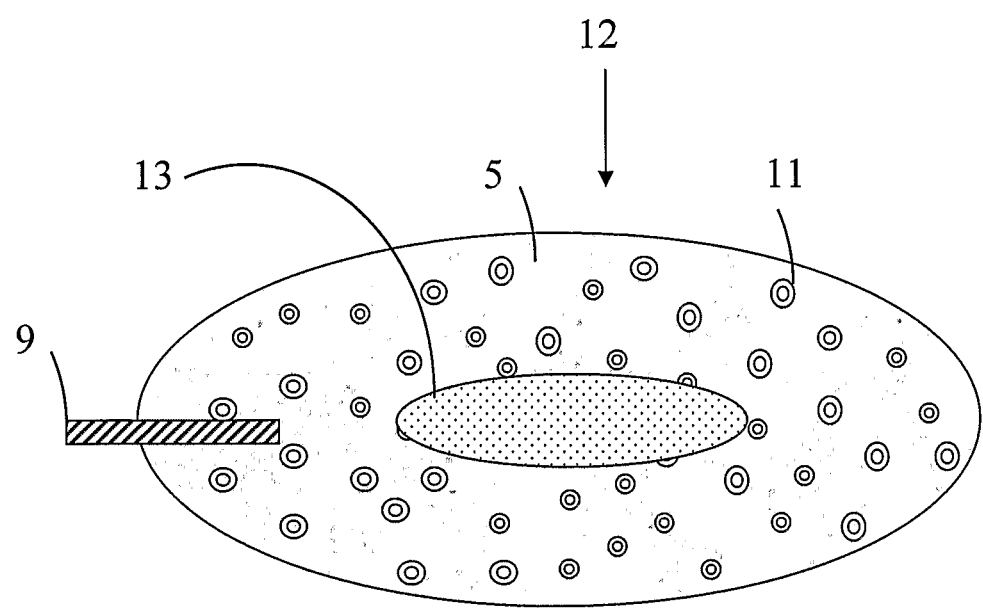
FIG. 2 is a cross sectional view of an abrasive confectionery product having a powder center according to one embodiment of the invention.

FIG. 2 illustrates a cross sectional view of an abrasive confectionery product having a powder center according to another embodiment of the invention, which is designated as numeral 12. Confectionery product 12 comprises base confectionery material 5; a plurality of microcapsules 11 containing an inert sugar core, wherein the microcapsules 11 are substantially uniformly dispersed throughout base material 5; a powder center 13 containing a health enhancing agent and an effervescent agent; and optionally, stick 9 embedded within base material 5 when confectionery product 12 is a lollipop. Since the microcapsules 11 are uniformly dispersed throughout base material 5, they are exposed to the oral cavity as abrasive inclusions as base material 5 is incrementally dissolved. Further, as the base material 5 dissolves, saliva from the oral cavity contacts the powder center 13 causing the powder to effervesce and promoting contact of the health enhancing agent with surfaces within the oral cavity. An exemplary health enhancing agent may be a herbal product such as eucalyptus.

Figure 3:
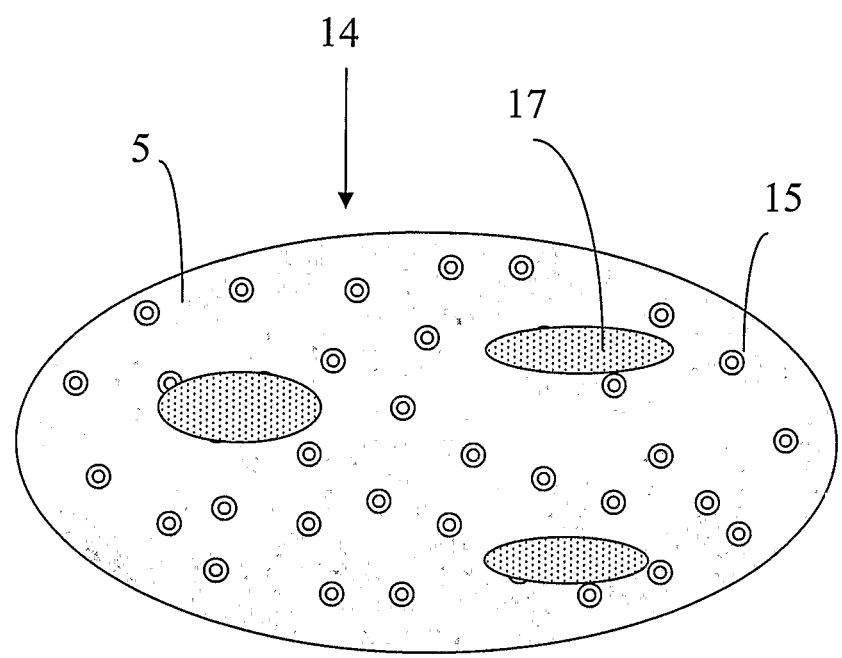
FIG. 3 is a cross sectional view of an abrasive confectionery product having powder compartments according to one embodiment of the invention.

FIG. 3 illustrates a cross sectional view of a uniformly abrasive confectionery product having powder compartments according to another embodiment of the invention, which is designated as numeral 14. Confectionery product 14 comprises base confectionery material 5; a plurality of microcapsules 15 containing a first health enhancing agent, wherein the microcapsules 15 are substantially uniformly dispersed throughout base material 5; and powder compartments 17 containing a second health enhancing agent and an effervescent agent. Since the microcapsules 15 are uniformly dispersed throughout base material 5, they are exposed to the oral cavity as abrasive inclusions as base material 5 is incrementally dissolved. The first health enhancing agent is contained within microcapsules which dissolve in the oral cavity or which dissolve in the gastrointestinal tract, depending on the intended site of absorption and/or activity of the first health enhancing agent. Further, as the base material 5 dissolves, saliva from the oral cavity contacts the powder compartments 17 causing the powder to effervesce and promoting contact of the second health enhancing agent with surfaces within the oral cavity.

Microcapsules

In a currently preferred embodiment, the abrasive inclusions comprise microcapsules. In one embodiment, the abrasive inclusions consist essentially of microcapsules.

Microcapsules consist of a shell and a core, wherein the core contains the microencapsulated materials. The shell is formed from a hardened material and is produced using a microencapsulation technique as is well known to those skilled in the art of pharmaceutical compositions. The shell is sufficiently hardened to provide an abrading action, yet will not damage or cause pain to the tongue. Non-limiting examples of materials which may be used for the shell include waxes, shellac, starch, zein protein, acrylic polymers such as ethylacrylate and methacrylic acid copolymers, cellulose derivatives, such as ethyl cellulose, methylcellulose, hydroxypropyl methylcellulose, carboxymethylcellulose and combinations of any of the aforementioned. In particular, combinations of hydrophilic and hydrophobic materials may be used for the shell.

In one embodiment, the shell comprises a combination of hydroxypropyl methylcellulose and ethyl cellulose. Conveniently, the hydroxypropyl methylcellulose may be used at 5 to 50% of the coating mixture and the ethyl cellulose may be used at 15 to 40% of the coating mixture.

Solvents used for forming the shell typically include organic solvents such as acetone and methanol, as well as water, depending on the material being encapsulated. Organic solvents are typically used at a concentration of 70 to 95%, for example 80 to 93%, of the coating mixture, whereas water-based solvents are typically used at a concentration of 20 to 50% of the coating mixture.

In particular, the materials selected to form the microcapsule shell enable the microcapsule to retain its integrity under the high temperature conditions of the confectionery production process e.g. 70° C. to 130° C., and yet renders the microcapsule capable of dissolving under conditions present in the oral cavity, e.g. temperature of 30° C. to 40° C. Furthermore, the shell acts as a thermal barrier for materials encapsulated therein, such as a heat-sensitive health enhancing agent.

The heat-resistant property of the microcapsule shell enables incorporation into the confectionery product of health enhancing agents which are generally susceptible to degradation or inactivation upon exposure to heat, and which in the absence of the microcapsule shell would be rendered inactive if exposed to the temperatures used for producing the confectionery product. Further, the use of such heat-resistant microcapsules enables their incorporation into the base confectionery material in a substantially uniformly dispersed manner. That is, in order to disperse the microcapsules into the base material in a substantially uniform manner, the base material must be in a heated pliable state, thus enabling thorough mixing and distribution of the microcapsules throughout.

In a particular embodiment, the shell of the microcapsule remains intact within the oral cavity and is capable of dissolving under conditions present in the gastrointestinal tract, for example at the pH present in the stomach or small intestine.

The coating of the microcapsule is typically applied at a level of about 5 to about 50% by weight, with coating levels on the order of about 15 to about 30 weight percent being typical. It is well within the ability of those of skill in the art to vary the combinations of coating materials and the percentages thereof according to the properties and characteristics of the material being microencapsulated. Coating is generally effected using apparatus known in the art, for example, a fluidized bed, using known techniques such as the Wurster coating process.

There is no particular limitation on the shape of the microcapsules. In particular embodiments, the microcapsules have a shape selected from the group consisting of spherical and ellipsoid. Ellipsoid shapes have at least one axis elongated as compared to the other two axes, and include for example oblate (disc-like) and prolate (cigar-like) spheroids. When ellipsoid, the elongated axis of the microcapsule may be referred to as the major axis. The diameter or major axis of the microcapsule has a length ranging from 100 to 900 microns or between about 70 and 500 microns, or between about 50 and 400 microns.

The material encapsulated within the microcapsule and surrounded by the shell may be referred to as the "core". The core preferably comprises a health enhancing agent, optionally in combination with additives which facilitate the coating, dissolution or absorption properties of the health enhancing agent. Alternately or in addition, the microcapsule core may comprise inert substances, also termed an inert substrate, such as a sugar. In some cases, only inert substances will form the core. Inert substrates can be formed of various materials known in the art, for example: sugars, such as lactose, sucrose or dextrose; polysaccharides, such as maltodextrin or dextrates; starches; cellulosics, such as microcrystalline cellulose; inorganics, such as dicalcium phosphate, hydroxyapitite, tricalcium phosphate or talc; and polyols, such as mannitol, xylitol, sorbitol or cyclodextrin.

The encapsulated material is generally in the form of a fine powder or multiparticulate preparation. A powder constitutes a finely divided (milled, micronized, nanosized, precipitated) form of the material, for example a mixture of a health enhancing agent and additives.

In some cases, the health enhancing agent to be encapsulated will be in a liquid form, for example an emulsion of a hydrophobic pharmaceutical agent. Accordingly, the liquid may be absorbed onto a carrier and then converted to a powder form prior to microencapsulation. Examples of suitable carriers include without limitation starch, porous starch, microcrystalline cellulose, maltodextrin, calcium phosphate and calcium carbonate.

The microcapsules can optionally include one or more additives, either in the shell, or as part of the core. Additives include without limitation, antioxidants, binders, buffers, chelating agents, diluents, disintegrants, fillers, lubricants, plasticizers, preservatives, solublilizers, solvents, surfactants, and sweeteners, as is known in the art. Specific materials may fulfill the function of more than one category of additive. The particular additives and their amounts can be readily determined by one of skill in the art.

In a particular embodiment, the microcapsules of the invention include a plasticizer in the shell. Plasticizers include without limitation, polyethylene glycol, triethyl citrate, ethyl citrate, dibutyl sebacate, diethyl phthalate, glycerin, triacetin, propylene glycol castor oil and sorbitol.

The microcapsule shell may be preferably coated with sugar or a substance flavored to have substantially the same taste as the base material.

More that one type of microcapsule may be incorporated into the confectionery product, for example, a first type of microcapsule formulated to dissolve in the oral cavity, and a second type of microcapsule formulated to dissolve in the gastrointestinal tract. In this way, the confectionery product can deliver different health enhancing agents to different sites of action or absorption. For example, a single confectionery product may contain a first type of microcapsule formulated to dissolve in the mouth and release a herbal extract which freshens the breath, and a second type of microcapsule formulated to dissolve in the gastrointestinal tract and release a vitamin intended for absorption in the small intestine. Alternately, a single confectionery product may contain a first type of microcapsule containing a first health enhancing agent, and a second type of microcapsule containing a second health enhancing agent, but the distinct types of microcapsules may be formulated so as to both dissolve in the mouth, or to both dissolve in the gastrointestinal tract.

Health Enhancing Agents

The health enhancing agent may be a pharmaceutical active agent or a natural product such as a herbal extract. The health enhancing agent may be one which has activity in reducing, preventing or treating a disorder of the oral cavity. Disorders of the oral cavity include without limitation, candidiasis, halitosis (also referred to as oral malodor), herpes simplex, lichen planus, leukoplakia, stomatitis (including aphthous stomatitis) and xerostomia. Alternately, the health enhancing agent may be associated with other indications or beneficial effects. The health enhancing agent may be selected from an analgesic agent, an antibacterial agent, an antiseptic agent, a cholinergic agent, an antifungal agent, a steroid, a nutritional supplement, an ethereal oil, a vitamin, a plant product and combinations thereof.

Exemplary analgesic agents include, without limitation, paracetamol, non-steroid anti-inflammatory drugs, salicylates, ibuprofen and lidocaine. Exemplary antibacterial agents include, without limitation, dichlorobenzyl alcohol, amylmetacresol and antibiotics. Exemplary antibiotics include penicillins carbapenems, cephalosporins aminoglycosides, bacitracin, gramicidin, mupirocin, chloramphenicol, thiamphenicol, lincomycin, clindamycin, macrolides, novobiocin, polymyxins, rifamycins, spectinomycin, tetracyclines, vancomycin, teicoplanin, streptogramins, anti-folate agents, sulfonamides, trimethoprim, pyrimethamine, nitrofurans, methenamine mandelate, methenamine hippurate, nitroimidazoles, quinolones, fluoroquinolones, isoniazid, ethambutol, pyrazinamide, para-aminosalicylic acid, cycloserine, capreomycin, ethionamide, prothionamide, thiacetazone and viomycin. Exemplary antiseptics include, without limitation, chlorhexidine and salts thereof, benzalkonium and salts thereof, triclosan and cetylpyridium chloride. Exemplary cholinergic agents include, without limitation, pilocarpine and cevimeline. Exemplary antifungal agents include, without limitation, tolnaftate, miconazole, fluconazole, clotrimazole, econazole, ketoconazole, itraconazole, terbinafine, amphotericin, nystatin and natamycin. Exemplary steroids include, without limitation, prednisone acetate, prednisone valerate, prednisolone, aclometasone dipropionate, fluocinolone acetonide, dexamethasone, methylprednisolone, desonide, pivolate, clocortolone pivolate, triamcinolone acetonide, prednicarbate, fluticasone propionate, flurandrenolide, mometasone furoate, desoximetasone, betamethasone, betamethasone dipropionate, betamethasone valerate, betamethasone propionate, betamethasone benzoate, diflorasone diacetate, fluocinonide, halcinonide, amcinonide, halobetasol propionate, and clobetasol propionate. Nutritional supplements include without limitation, vitamins, minerals, herbal products and amino acids. Vitamins include without limitation, vitamin A, those in the vitamin B family, vitamin C, those in the vitamin D family, vitamin E and vitamin K. Ethereal oils include without limitation, those derived from mint, sage, fir, lavender, basil, lemon, juniper, rosemary, eucalyptus, marigold, chamomile, orange and the like. In addition to the aforementioned, plant products include without limitation, kava (*Piper methysticum*), purple coneflower (*Echinacea* sp.), horsetail (*Equisetum arvense*), myrrh (*Commiphora myrrha*), agrimony (*Agrimonia* sp.), cat's claw (*Uncaria tomentosa*), thuja (*Thuja* sp.), propolis, poke root (*Phytolaccae radix*), elecampane (*Inula helenium*) and goldenseal (*Hydrastis canadensis*).

More than one health enhancing agent may be incorporated into the confectionery product. For example, a heat sensitive health enhancing agent may be contained in the core of the microcapsules, while a different less sensitive health enhancing agent may be contained in another compartment of the product, such as a powder compartment or a powder center. Alternately or in addition, a first health enhancing agent may be contained in the core of a first microcapsule formulated to dissolve in the oral cavity, while a second health enhancing agent may be contained in the core of a second microcapsule formulated to dissolve in the gastrointestinal tract. The first health enhancing agent may be intended for delivery to the oral cavity for treatment of a disorder therein, such as halitosis, herpes simplex, xerostomia, candidiasis, stomatitis, leukoplakia or lichen planus. The health enhancing agent may be intended for delivery to the general circulation for maintenance of optimal health, as in the case of a vitamin or mineral.

FIG. 1 illustrates one embodiment of the invention wherein the abrasive inclusions contain a health enhancing agent within the core.

FIG. 2 illustrates one embodiment of the invention wherein the abrasive inclusions consist essentially of microcapsules containing an inert core, and a powder center contains a health enhancing agent, together with an effervescent agent.

FIG. 3 illustrates one embodiment of the invention wherein the abrasive inclusions contain a first health enhancing agent within the core, and powder compartments contain a second health enhancing agent together with an effervescent agent.

Figure 4:
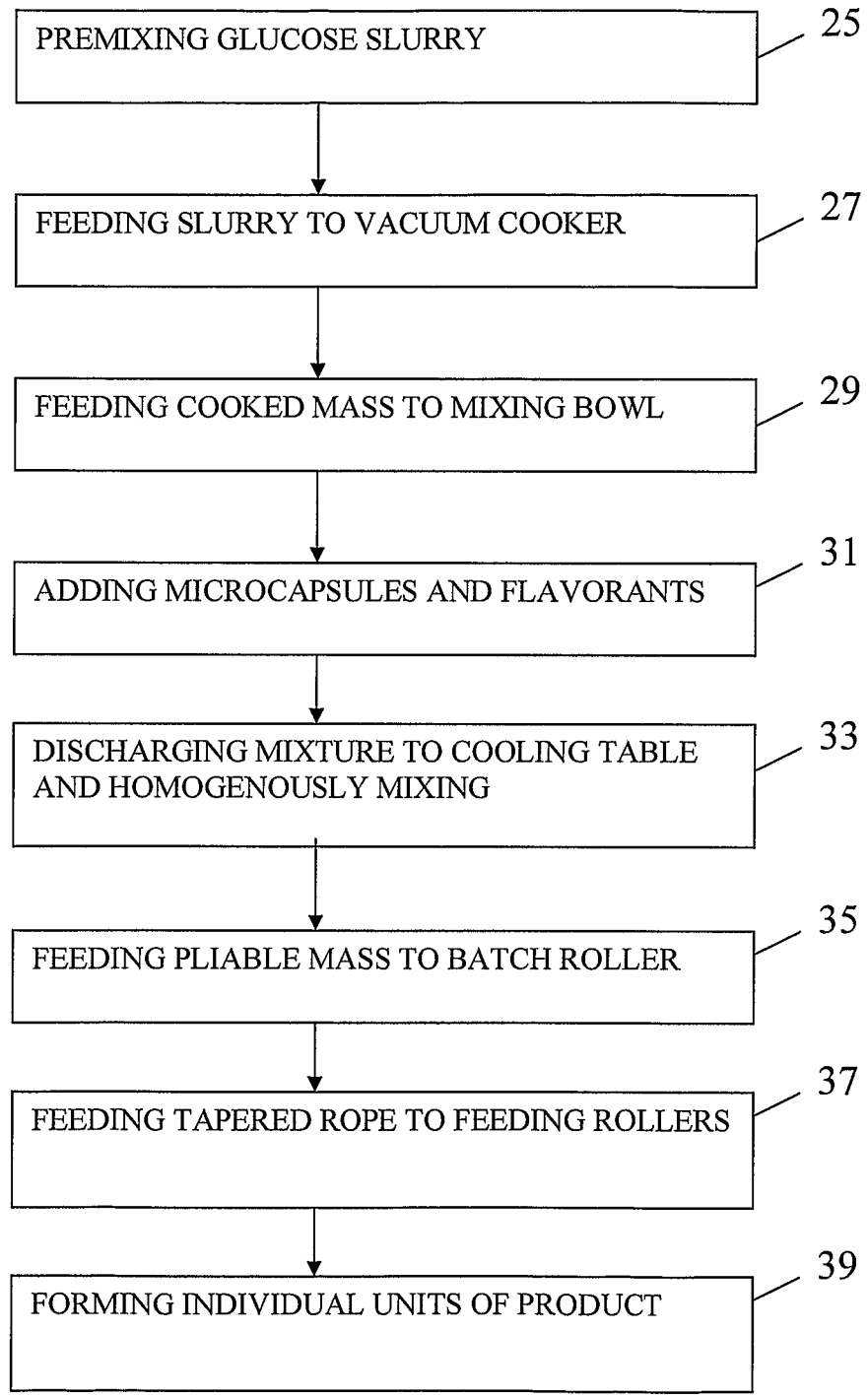
FIG. 4 is a flow chart that illustrates a process for producing an abrasive confectionery product, according to one embodiment of the invention.

FIG. 4 illustrates a process for producing a uniformly abrasive confectionery product, according to one embodiment of the invention. In step 25, sugar and glucose are continuously pre-mixed together with water at a temperature of approximately 110° C. and under controlled conditions, to ensure a predetermined ratio of sugar to glucose. The glucose slurry is then fed in step 27 to a vacuum cooker in which the mixture is first boiled within a spiral tube immersed in steam heated to a temperature of approximately 142° C., an optimal temperature for producing boiled sugar confectionery products, and the boiled mass is then subjected to a vacuum for a period of approximately 5 minutes, to cause water present in the mixture to vaporize so that its moisture level will be less than 1% and that the confectionery product will be less susceptible to absorb moisture from the surroundings. Colorants may be added to the mixture while vacuum is being applied thereto.

The cooked mass is then fed to a mixing bowl in step 29. At this stage the cooked mass is not subjected to heat and its temperature decreases to approximately 100-120° C. Materials to be incorporated into the cooked mass are added in step 31. These materials include microcapsules, for example those containing vitamin C in the core; flavorants, for example peppermint, menthol or lemon; and optionally an acidulent such as citric acid. Colorants may also be added at this step, for example if they were not previously added. The whole mixture is briefly mixed (approximately one minute), in the mixing bowl.

In step 33 the mixture is discharged to a means for cooling and kneading, such as a cooling table, a cooling drum, or any other means for cooling and kneading edible products well known to those skilled in the art. At this step, the confectionery product mixture is cooled to and maintained at a temperature of approximately 70-90° C. by circulation of cooled atmospheric air or chilled liquid (conveniently water) throughout the means. Maintenance of the temperature at that level ensures that the mixture will remain sufficiently pliable to enable thorough mixing, but that flavorants will not evaporate. It is further important that at this step that the mass is cooled evenly so that it is sufficiently homogenous and plastic to ensure even feeding to the machines in the subsequent steps. The means is adapted for kneading and homogenously mixing the materials transferred thereto. For example, it may comprise a mixing vessel with a kneading hook affixed therein wherein the vessel is mounted on a platform which may be simultaneously rotated and articulated at an angle. In this manner, the confectionery product mixture may be kneaded, with outer cooler layers continuously moved into the hotter center of the mass thereby producing a homogeneous mixture in which the microcapsules and other ingredients are substantially uniformly distributed therein. The pliable and mixed mass is fed to a batch roller in step 35. A batch roller, as well known to those skilled in the art, is adapted to roll the pliable mass to a large sausage or conical shape and to cause the same to have tapered ends in a rope shape. In step 37 the tapered rope is fed to a series of feeding rollers, which are sometimes referred to as rope sizers, for reducing the rope to a desired size. The size-reduced rope is fed to a forming machine in step 39, wherein individual units are formed, compressed to a desired shape, and discharged to a cooling conveyor. When the confectionery product is a lollipop; e.g. 800 of which can be formed per minute, a stick is fed into the mass fed into the forming machine. The cooling conveyor cools the confectionery products while they are being rotated to ensure that they remain round. The cooled confectionery products are then forwarded to a wrapping station, e.g. whereat they are wrapped in a cellophane wrapper.

In order to confirm that added microcapsules are evenly distributed throughout a confectionery base material, a boiled mass may be prepared as previously described, with the exception that no colorants are added at steps 27 to 31, resulting in a substantially transparent base material having a very light yellow color. Incorporation of the microcapsules throughout the confectionery base material in a substantially uniform manner by the end of step 33 may be confirmed by visual inspection of the mixed mass. It will be appreciated that the process for producing a non-caloric or toffee confectionery product is similar to a boiled sugar confectionery product, with the exception of the pre-mixing and vacuum cooking steps.

Figure 5:
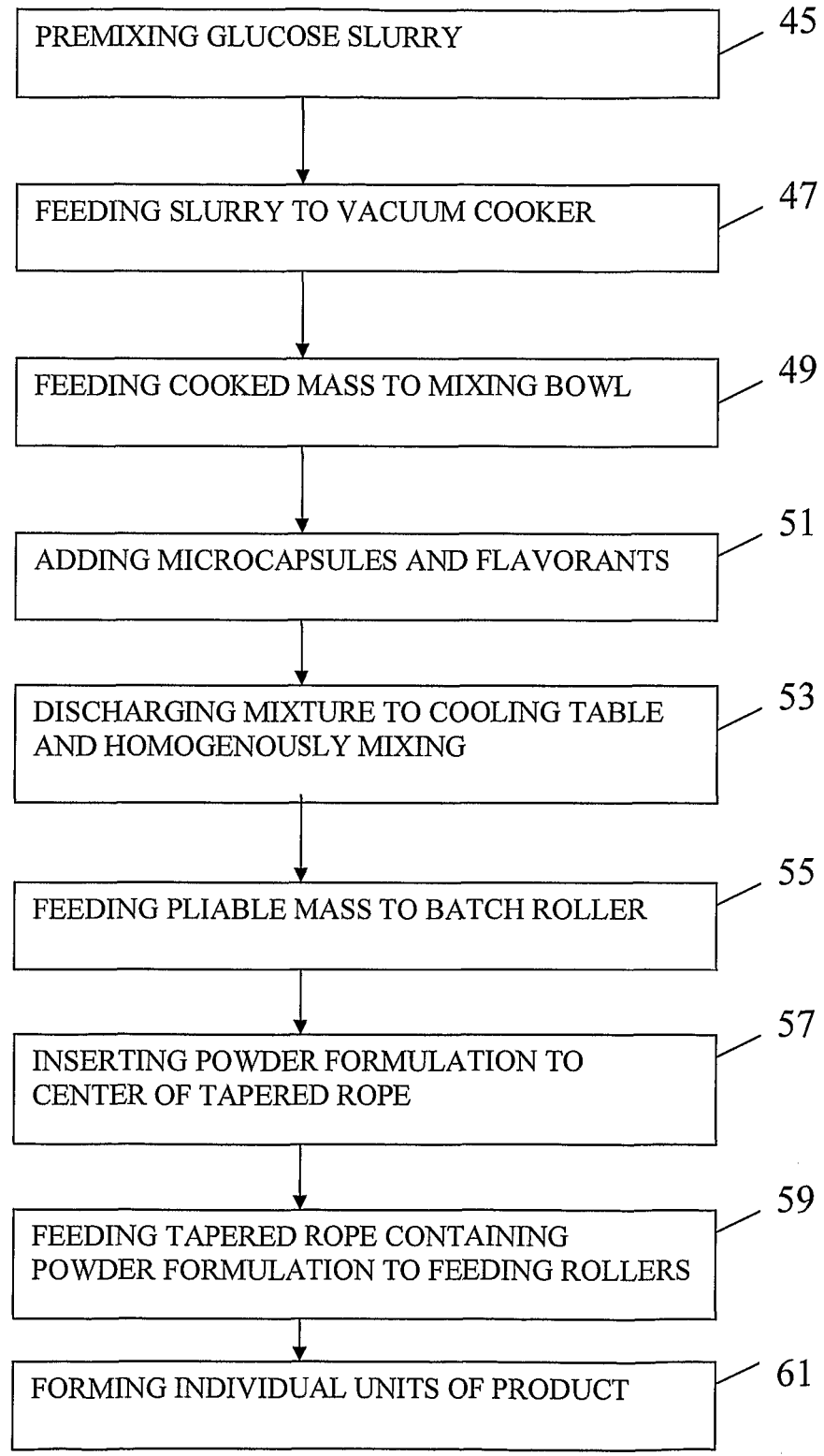
FIG. 5 is a flow chart that illustrates a process for producing an abrasive confectionery product having a powder center, according to one embodiment of the invention.

FIG. 5 illustrates a process for producing a uniformly abrasive confectionery product having a powder center, according to another embodiment of the invention. In this embodiment, steps 45 through 55 are essentially identical to steps 25 through 35 respectively of the embodiment illustrated in FIG. 4. In the embodiment illustrated in FIG. 5, the microcapsules may or may not contain a health enhancing agent. In step 57, a powder formulation comprising an effervescent agent is inserted to the center of the tapered rope containing the microcapsules. The powder is inserted along the longitudinal axis of the tapered using a means for powder dosing such as a powder dosing machine. The powder dose is controlled so that a predetermined and fixed amount of powder is inserted per unit length of the rope. The powder formulation may or may not comprise a health enhancing agent. In step 59 the tapered rope containing the powder formulation is fed to a series of feeding rollers, which are sometimes referred to as rope sizers, for reducing the rope to a desired size. In step 61 the size-reduced rope is fed to a forming machine wherein individual units are formed, compressed to a desired shape, and discharged to a cooling conveyor.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

In order that this invention may be better understood, the following examples are set forth. These examples are for the purpose of illustration only and are not to be construed as limiting the scope of the invention in any manner.

EXAMPLES

Example 1

Formulations of Confectionery Base Materials

A formulation for producing a boiled sugar confectionery base material is shown in Table 1. The ingredients are cooked together at 140 to 142° C. Citric acid may be added following cooking.

TABLE 1

Boiled sugar confectionery base material

| Ingredient | Amount (kg) |
|---|---|
| Glucose 80% solution | 48.78 |
| Water | 19.23 |
| Sugar | 60.0 |

A formulation for producing a toffee confectionery base material is shown in Table 2. The ingredients are cooked together at 120 to 121° C. Citric acid may be added following cooking.

TABLE 2

Toffee confectionery base material

| Ingredient | Amount (kg) |
|---|---|
| Palm kernal oil | 14.0 |
| Lecithin | 0.3 |
| Glucose 80% solution | 64.71 |
| Fondant | 2.1 |
| Water | 13.44 |
| Sugar | 52.25 |

A formulation for producing a sugar-free candy confectionery base material is shown in Table 3. The ingredients are cooked together at 155 to 160° C. Citric acid may be added following cooking.

TABLE 3

Sugar-free candy confectionery base material

| Ingredient | Amount (kg) |
|---|---|
| Isomalt | 75.0 |
| Water | 24.0 |
| Non-sugar sweetener | 0.05-0.10 |

While certain embodiments of the invention have been illustrated and described, it will be clear that the invention is not limited to the embodiments described herein. Numerous modifications, changes, variations, substitutions and equivalents will be apparent to those skilled in the art without departing from the spirit and scope of the present invention as described by the claims, which follow.

The invention claimed is:

1. A consumable abrasive confectionery product comprising a consumable, hardened base confectionery material with a stick or handle embedded within the hardened base material and a plurality of abrasive microcapsules substantially uniformly dispersed throughout the base material, said microcapsules comprising a shell and an inert core, the inert core consisting of an inert substrate wherein said inert substrate comprises tricalcium phosphate, the shell made from a combination of hydrophobic and hydrophilic materials, the hydrophilic materials comprising 5% to 50% of the shell by weight, the shell comprising a material selected from the group consisting of wax, shellac, starch, zein protein, ethyl cellulose, methylcellulose, hydroxypropyl methylcellulose, ethylacrylate, methacrylic acid copolymers and combinations thereof, wherein the microcapsules has a coating level in the range of about 5 to about 30 weight percentage of the microcapsules, the shell being resistant to degradation upon exposure to temperature in the range from about 70° C. to about 130° C. and being capable of dissolving upon exposure to temperature in the range from about 30° C. to about 40° C., and wherein the abrasive microcapsules are configured to efficiently abrade tongue surface and/or other soft oral cavity surfaces.

2. The confectionery product of claim 1, wherein the abrasive microcapsules are dissolvable in at least one of the oral cavity and the gastrointestinal tract.

3. The confectionery product of claim 1, further comprising a health enhancing agent, wherein the health enhancing agent is a pharmaceutical agent or a natural product.

4. The confectionery product of claim 1, wherein the shell is sufficiently hardened to provide an abrading action with respect to a tongue surface without causing damage or pain to the tongue surface.

5. The confectionery product of claim 3, wherein the health enhancing agent has activity in reducing, preventing or treating a disorder of the oral cavity, wherein the disorder of the oral cavity is selected from the group consisting of candidiasis, halitosis, herpes simplex, lichen planus, leukoplakia, stomatitis and xerostomia.

6. The confectionery product of claim 3, wherein the health enhancing agent is selected from the group consisting of an analgesic agent, an antibacterial agent, an antiseptic agent, a cholinergic agent, an antifungal agent, a steroid, a nutritional supplement, an ethereal oil, a vitamin, a plant product and combinations thereof.

7. The confectionery product of claim 1, wherein the inert substrate further comprises an additional inert substrate selected from the group consisting of starch, microcrystalline cellulose, dicalcium phosphate, hydroxyapitite, talc, and combinations thereof.

8. The confectionery product of claim 1, selected from the group consisting of a consumable boiled sugar confectionery product, and a non-caloric or reduced calorie consumable confectionery product.

9. The confectionery product of claim 1, further comprising a powder compartment, wherein the powder compartment comprises an effervescent agent, selected from the group consisting of sodium bicarbonate, potassium bicarbonate, sodium carbonate, potassium carbonate, calcium carbonate, ammonium carbonate and combinations thereof.

10. The confectionery product of claim 9, wherein the powder compartment is a powder center.

11. The confectionery product of claim 10, further comprising at least one health enhancing agent, contained in the powder center.

12. The confectionery product of claim 11, wherein different health enhancing agents are contained in the powder center.

13. The confectionery product of claim 1, wherein the confectionery product is a lollipop.

14. A process for producing the abrasive confectionery product according to claim 1, the process comprising: step (a) thoroughly mixing together the abrasive microcapsules and the base material so as to disperse the abrasive microcapsules throughout said base material in a substantially uniform manner, wherein said base material is in the form of a cooked mass, and wherein the mixing is carried out while the base material is maintained at a temperature in the range of 70° C. to 90° C., thereby providing a base material having the abrasive microcapsules substantially uniformly dispersed therein.

15. The process for producing the abrasive confectionery product of claim 9, the process comprising: step (a) thoroughly mixing together the abrasive microcapsules and the base material so as to disperse the abrasive microcapsules throughout said base material in a substantially uniform manner, wherein said base material is in the form of a cooked mass, and wherein the mixing is carried out while the base material is maintained at a temperature in the range of 70° C. to 90° C.; and step (b) inserting a powder formulation to at least one region of the base material having the abrasive microcapsules substantially uniformly dispersed therein.

16. The process of claim 15, wherein the at least one region is the center region.

17. The process of claim 15, wherein at least one health enhancing agent is contained in the powder formulation.

18. The process of claim 17, wherein different health enhancing agents are contained in the powder formulation.

* * * * *